United States Patent
Bezenger et al.

(10) Patent No.: US 8,449,932 B2
(45) Date of Patent: May 28, 2013

(54) GROWTH OF BIFIDOBACTERIA IN FERMENTED MILK PRODUCTS

(75) Inventors: Marie-Claude Bezenger, Bruyères-le-Chatel (FR); Jean-Marie Odinot, Remereville (FR); Cécile Seimandi, St Germain lés Arpajon (FR)

(73) Assignee: Chr. Hansen A/S, Horsholm (DK)

( * ) Notice: Subject to any disclaimer, the term of this patent is extended or adjusted under 35 U.S.C. 154(b) by 435 days.

(21) Appl. No.: 12/602,624

(22) PCT Filed: Jun. 6, 2008

(86) PCT No.: PCT/EP2008/004528
§ 371 (c)(1),
(2), (4) Date: Feb. 15, 2010

(87) PCT Pub. No.: WO2008/148561
PCT Pub. Date: Dec. 11, 2008

(65) Prior Publication Data
US 2010/0189841 A1 Jul. 29, 2010

(30) Foreign Application Priority Data
Jun. 6, 2007 (EP) .................................... 07109708

(51) Int. Cl.
*A23C 9/12* (2006.01)

(52) U.S. Cl.
USPC ................. 426/43; 426/34; 426/42; 426/583

(58) Field of Classification Search
CPC ...................................................... A23C 9/1234
USPC ............................... 426/34, 42, 43, 580, 583
See application file for complete search history.

(56) References Cited

U.S. PATENT DOCUMENTS

| 4,187,321 A | 2/1980 | Mutai et al. |
| 4,588,595 A | 5/1986 | Okonogi et al. |
| 5,230,912 A | 7/1993 | Yajima et al. |
| 2005/0031735 A1 | 2/2005 | Serata et al. |

FOREIGN PATENT DOCUMENTS

| EP | 0 111 392 B1 | 4/1988 |
| WO | WO 98/54337 | 12/1998 |

OTHER PUBLICATIONS

A.B. Martin-Diana et al., "Development of a fermented goat's milk containing probiotic bacteria", International Dairy Journal 13 (2003) 827-833.
M. Saxelin et al., "The technology of probiotics", Trends in Food Science & Technology 10 (1999) 387-392.

*Primary Examiner* — Leslie Wong
(74) *Attorney, Agent, or Firm* — Foley & Lardner, LLP

(57) ABSTRACT

A method for the preparation of a fermented milk product comprising Bifidobacteria and *Streptococcus thermophilus* bacteria, wherein the *Streptococcus thermophilus* bacteria improve the growth of the Bifidobacteria during the fermentation.

25 Claims, No Drawings

GROWTH OF BIFIDOBACTERIA IN
FERMENTED MILK PRODUCTS

This application is a 371 of PCT/EP2008/004528, filed Jun. 6, 2008.

FIELD OF INVENTION

The present invention relates to the improvement of growth of Bifidobacteria by selected bacterial strains in fermented milk products.

BACKGROUND OF INVENTION

Dairy products and specifically yogurt-like products form the largest segment by far of the market of probiotic products. Dairy products are excellent products for delivering useful probiotic bacteria such as Bifidobacteria and introducing them into the gastrointestinal tract.

The *Bifidobacterium* BB-12® is a well known probiotic bacterium. In the case of BB-12® the available clinical evidence indicates that at least $10^8$ cfu viable probiotic bacteria per gram fermented milk product is required. Accordingly, it is desirable to have at least $10^8$ cfu viable cells of probiotic bacteria per gram fermented milk product (e.g. a fermented milk yogurt product).

EP111392B1 discloses the selection of wild-type *Streptococcus thermophilus* strains having a relatively high oxygen level uptake ability thus improving the survival of a strictly anaerobic *Bifidobacterium* species when it is combined with the *Streptococcus* strain during fermentation of milk.

SUMMARY OF INVENTION

The problem to be solved by the present invention is to provide a method to improve growth of Bifidobacteria population in milk during the fermentation process for making fermented milk products (e.g. a yogurt) in order to obtain a high cell count of Bifidobacteria in the final product.

The solution is based on the surprising finding of the present inventors that a specific Streptococcus thermophilus ST6008 (DSM 18111) strain significantly improves the growth of Bifidobacteria during fermentation of the milk. By using this strain the resulting fermented milk product will contain more than $10^8$ cfu/g Bifidobacteria (directly after the fermentation). Consequently, it is not necessary to add extra Bifidobacteria after fermentation is terminated to obtain a product with $10^8$ cfu/g Bifidobacteria.

The inventors tested a series of different *S. thermophilus* (16 in total) and found that only the strain identified as *Streptococcus thermophilus* strain (ST6008) and deposited under DSM18111 significantly improves the growth of Bifidobacteria during the milk fermentation. As a matter of fact, some other strains of *Streptococcus thermophilus* influenced the growth of Bifidobacteria negatively.

In addition, the inventors surprisingly observed that ST6008 has a unique characteristic in that the strain can be added in very high amounts of cfu/g to the milk (and propagated to very high cell counts) without changing the products characteristics of the fermented milk, such as pH and post acidification. The other tested ST strains did not have this additional advantage.

Accordingly, a first aspect of the invention relates to a method for preparation of a fermented milk product, such as a product comprising at least $10^8$ cfu Bifidobacteria per gram fermented milk product, wherein the method comprises:
i) inoculating milk with a culture (such as a yogurt culture) comprising at least one *Streptococcus thermophilus* strain, at least one *Bifidobacterium* strain and optionally at least one *Lactobacillus bulgaricus* strain, wherein one of said *Streptococcus thermophilus* strain is selected from the group consisting of: *Streptococcus thermophilus* strain ST6008 with registration number DSM18111, a mutant of ST6008, and a variant of ST6008;
ii) fermenting the milk under suitable conditions; and
iii) optionally packaging a suitable amount of the fermented milk product in a suitable package. An interesting embodiment relates to a method for preparation of a fermented milk product comprising at least $10^8$ cfu Bifidobacteria per gram fermented milk product wherein the method comprises:
i) inoculating milk with a yogurt culture comprising at least one *Lactobacillus bulgaricus* strain, at least one *Streptococcus thermophilus* strain and at least one Bifidobacterium strain, wherein one of said *Streptococcus thermophilus* strain is *Streptococcus thermophilus* strain ST6008 with accession number DSM18111;
ii) fermenting the milk under suitable conditions to obtain a fermented milk product with at least $10^8$ cfu Bifidobacteria per gram fermented milk; and
iii) packaging a suitable amount of the fermented milk product in a suitable package.

A second aspect of the invention relates to the ST6008 strain and mutants/variants thereof, and to a culture (such as a starter culture) comprising a strain of the invention, optionally together with another strain, such as a *Bifidobacterium* strain (eg BB-12). An interesting composition comprises i) from $10^5$ to $10^{12}$ cfu/g BB-12 and ii) from $10^5$ to $10^{12}$ cfu/g ST6008.

DETAILED DISCLOSURE

The present invention relates to, in its broadest aspect, to a method for preparation of a fermented milk product, which comprises:
i) inoculating milk with a *Bifidobacterium* strain, and a *Streptococcus thermophilus* strain selected from the group consisting of: *Streptococcus thermophilus* strain ST6008 with deposit number DSM18111; a mutant of ST6008; and a variant of ST6008 (such as a mutant/variant strain which has one or more (preferably, all) of the characteristics of the *S. thermophilus* strain ST6008, e.g. the mutant and/or variant strain is able to promote the growth of a *Bifidobacterium* strain);
ii) fermenting the milk;
iii) optionally adding further microorganisms and/or additives to the fermented milk; and
iv) optionally packaging the fermented milk product. In a presently preferred embodiment, step i) further comprises inoculation of the milk with a *Lactobacillus bulgaricus* strain.

Another embodiment relates to a method for preparation of a fermented milk product, such as a product comprising at least $10^8$ cfu Bifidobacteria per gram fermented milk product, wherein the method comprises:
i) inoculating milk with a culture (such as a yogurt culture) comprising at least one *Streptococcus thermophilus* strain, at least one *Bifidobacterium* strain and optionally at least one *Lactobacillus bulgaricus* strain, wherein one of said *Streptococcus thermophilus* strain is selected from the group consisting of: *Streptococcus thermophi*-

*lus* strain ST6008 with registration number DSM18111, a mutant of ST6008, and a variant of ST6008;

ii) fermenting the milk under suitable conditions; and iii) optionally packaging a suitable amount of the fermented milk product in a suitable package.

Yet another embodiment relates to a method for preparation of a fermented milk product comprising at least $10^8$ cfu Bifidobacteria per gram fermented milk product wherein the method comprises:

i) inoculating milk with a yogurt culture comprising at least one *Lactobacillus bulgaricus* strain, at least one *Streptococcus thermophilus* strain and at least one *Bifidobacterium* strain, wherein one of said *Streptococcus thermophilus* strain is *Streptococcus thermophilus* strain ST6008 with accession number DSM18111;

ii) fermenting the milk under suitable conditions to obtain a fermented milk product with at least $10^8$ cfu Bifidobacteria per gram fermented milk; and iii) packaging a suitable amount of the fermented milk product in a suitable package.

The *Bifidobacterium* strain preferably belongs to a species selected from the group consisting of *Bifidobacterium adolescentis*, *Bifidobacterium animalis*, *Bifidobacterium asteroids*, *Bifidobacterium bifidum*, *Bifidobacterium breve*, *Bifidobacterium catenulatum*, *Bifidobacterium infantis*, *Bifidobacterium lactis*, *Bifidobacterium longum* and *Bifidobacterium pseudocatenulatum*, and it is presently preferred that the *Bifidobacterium* strain is a strain of *Bifidobacterium animalis* subspecies *lactis*. Examples of strains are strains selected from the group consisting of CHCC5445 (BB-12) with accession number DSM15954, CHCC7158 (HNO19, deposit number DSM17280), *Bifidobacterium* strain deposited as ATCC 27536, *Bifidobacterium infantis* strain Bbi99 (DSM 13692), BB-420, BI-04, CHCC2037, LAFTI B-94, DN 173 010, STB-2938, R0071, R0175, and BB-46, and a mutant of any of these strains.

In a useful embodiment, the obtained fermented milk product contains at least $10^8$ cfu Bifidobacteria per gram fermented milk product at end of fermentation, and/or the fermented milk product contains at least $10^8$ cfu/g Bifidobacteria after 28 days of storage at +6° C.

According to an important embodiment of the present method, the milk in step i) is inoculated with $10^5$ to $3 \times 10^2$ cfu/g of the *Bifidobacterium* and/or with $10^4$ to $3.5 \times 10^8$ cfu/g of the *Streptococcus thermophilus*. The milk may be inoculated simultaneously with the bacterial species. This is conveniently done by inoculating the milk with a starter culture comprising both bacterial species.

In yet an embodiment, the milk is further inoculated with at least one bacterial strain, such as a *Lactococcus lactis* subs. *lactis* strain (e.g. selected from the group consisting of *Lactococcus lactis* subs. *lactis* DN224; *Lactococcus lactis* subs. *lactis* DN223; and a mutant or variant strain of any of these). It is presently preferred that this extra helper organism is a *Lactococcus lactis* subs. *lactis* strain selected from the group consisting of *Lactococcus lactis* subs. *lactis* DN224, *Lactococcus lactis* subs. *lactis* DN223.

A product obtained by the present method of the invention may be defined as "yogurt", i.e. when the milk in inoculated with both a *Lactobacillus bulgaricus* strain and a *Streptococcus thermophilus* strain.

The fermented milk product (such as the yogurt) is conveniently packaged in a sealed package that contains from 25 to 3000 ml of the product, such as from 50 to 1000 ml.

The invention also relates to a culture (such as a starter culture) comprising from $10^5$ to $10^{12}$ cfu/g BB-12 and from $10^5$ to $10^{12}$ cfu/g ST6008. The culture may further comprise from $10^5$ to $10^{12}$ cfu/g of DN224 or DN223.

A further aspect of the present invention relates to a fermented milk product obtainable by the method of the invention, and to a fermented milk product comprising a *Streptococcus thermophilus* strain selected from the group consisting of ST6008 (DSM18111); a mutant of ST6008; and a variant of ST6008. It is presently preferred that the fermented milk product of the invention comprises $10^3$ to $10^{18}$ cfu/g of the *Streptococcus thermophilus* strain. The fermented milk product of the present invention may further comprise $10^3$ to $10^{10}$ cfu/g of Bifidobacteria and/or from $10^3$ to $10^{10}$ cfu/g of a *Lactococcus lactis* subs. *lactis* strain (such as DN224 or DN223).

In a last aspect, the present invention relates to a *Streptococcus thermophilus* strain selected from the group consisting of ST6008 (DSM18111), a mutant of ST6008 and a variant of ST6008 (such as a mutant/variant strain which has one or more (preferably, all) of the characteristics of the *S. thermophilus* strain ST6008, e.g. the mutant/variant strain is able to promote the growth of a *Bifidobacterium* strain (esp. BB-12). The strain may be in isolated form, e.g. substantially free of other bacterial strains.

*Bifidobacterium*

In a preferred embodiment the *Bifidobacterium* is at least one *Bifidobacterium* selected from the group consisting of *Bifidobacterium adolescentis*, *Bifidobacterium animalis*, *Bifidobacterium asteroids*, *Bifidobacterium bifidum*, *Bifidobacterium breve*, *Bifidobacterium catenulatum*, *Bifidobacterium infantis*, *Bifidobacterium lactis*, *Bifidobacterium longum* and *Bifidobacterium pseudocatenulatum*. A mixture comprising two or more of these listed strains may also be used.

In the preferred embodiment of the method the *Bifidobacterium* strain is a strain of *Bifidobacterium animalis* subspecies *lactis*. In particular, wherein the strain is *Bifidobacterium animalis* subspecies *lactis* strain BB-12 (CHCC5445) deposited under accession number DSM15954.

Another preferred *Bifidobacterium animalis* subspecies *lactis* strain is strain HNO19 (also known as DR10™ or HOWARU™). The strain was isolated from a commercial available infant formula product labeled Fernleaf DR-10 bifidus that was sold in Taiwan during 2000. It has the accession number CHCC7158 in the Hansen culture collection and is deposited with DSMZ under accession number DSM17280.

Measuring cfu/g of Bifidobacteria

Measuring the Bifidobacteria cfu/g cell count is done by quantifying the number of Colony Forming Units (cfu) in serial dilutions of the fermented product by colony counting on agar plates, according to standard methods in the art. Suitable medium and incubation are as given below:

Medium: MRS (de Man et al. 1960. J. Appl. Bacteriol. 23:130) no acid+1% dicloxacilline (SIGMA D-9016)+ 1% cystein (MERCK no. 2839); and Incubation: 3 days at 37° C. in anaerobic conditions As discussed herein use of ST6008 provides the possibility of obtaining more than $10^8$ cfu/g Bifidobacteria directly from the growth of Bifidobacteria during the fermentation. Accordingly, the at least $10^8$ cfu/g Bifidobacteria of step ii) of the first aspect relates to the cfu/g Bifidobacteria obtained directly after fermentation.

As shown in the working examples, the *Bifidobacterium* BB-12 has a good survival rate when grown together with ST6008.

Accordingly, in a preferred embodiment, the fermented milk product has at least $10^8$ cfu/g Bifidobacteria after 1 day of storage at +6° C., more preferred at least $10^8$ cfu/g Bifidobacteria after 7 days of storage at +6° C., even more preferred at least $10^8$ cfu/g Bifidobacteria after 14 days of storage at +6° C., even more preferred at least $10^8$ cfu/g Bifidobacteria after 21 days of storage at +6° C. and most preferred at least $10^8$ cfu/g Bifidobacteria after 28 days of storage at +6° C.

Suitable Fermentation Conditions

Generally speaking, the skilled person knows suitable fermenting conditions to ferment milk with the herein relevant bacteria.

Herein suitable conditions are e.g. where the milk is inoculated with the bacteria and fermented at 38° C. to 43° C. with the optimum at 40° C., until reaching a pH of 4.4 to 4.6 (roughly after around 8 hours).

Cooling the milk to +6° C. stops the fermentation and growth of herein relevant bacteria such as Bifidobacteria.

In a preferred embodiment the herein described improved growth is obtained by inoculating from $10^5$ to $3 \times 10^7$ cfu/g of *Bifidobacterium*; and by inoculating simultaneously ST6008 in a concentration from $10^4$ to $3.5 \times 10^6$ cfu/g.

If desired, one may add extra bacteria (e.g. extra *Bifidobacterium*) at some point of interest (e.g. after the completion of the fermentation).

Fermented Milk Product

As is known to the skilled person various different fermented milk products can be obtained by fermentation of milk.

In a preferred embodiment the fermented milk product is a product selected from the group consisting of yogurt, drinking yogurt, stirred yogurt, set yogurt and a yogurt like drink, bitter milk, butter milk, sour cream, fresh cheese and cheese.

Fermented milk comprising at least $10^8$ cfu/g Bifidobacteria as described herein can also be used as a product additive to e.g. put into other edible food products such as curd cheeses, chocolates, juices, meat products and dried milk powder products for young infants.

*Lactobacillus bulgaricus*

In the present context the Lactobacillus bulgaricus may be any suitable (e.g. commercially available) *Lactobacillus bulgaricus* strain.

As is known to the skilled person, it may be inoculated in adequate amounts to obtain an adequate amount of *Lactobacillus bulgaricus* in the final fermented milk product.

Addition of Other Bacteria Species such as Helper Strains

In the method as described herein other bacteria of interest may be added. Such bacteria may be added during the fermentation or after the fermentation as such has ended.

Examples of such additional bacteria include a bacterium selected from the list consisting of *Lactococcus* and *Lactobacillus*.

A preferred *Lactobacillus* is *Lactobacillus acidophilus* strain as LA-5® (commercially available from Chr. Hansen A/S, Denmark).

As described in WO98/54337 (Chr. Hansen, granted as EP0985043 B1) a lactic acid bacterial helper organism that is defective in its pyruvate metabolism may be added during the fermentation to get a number of improvements, including improving the shelf life of the bacteria. The strains DN224 (deposited as DSM 11037) and DN223 (deposited as DSM 11036), which are defective in their pyruvate metabolisms, are described as examples of suitable bacterial helper organisms.

Accordingly, in a preferred embodiment a lactic acid bacterial helper organism that is defective in its pyruvate metabolism is also added to the milk in order to be fermented as described herein.

In a preferred embodiment the lactic acid bacterial helper organism is a bacterium selected from the group consisting of *Lactococcus lactis* subspecies lactis strain DN223 deposited under the accession No. DSM 11036 and *Lactococcus lactis* subspecies lactis strain DN224 (deposited under No. DSM 11037). Most preferably, the lactic acid bacterial helper organism is DN224.

An embodiment relates to a culture comprising:

i) from $10^5$ to $10^{12}$ cfu/g BB-12 and ii) from $10^5$ to $10^{12}$ cfu/g ST6008.

iii) from $10^5$ to $10^{12}$ cfu/g of DN224.

Deposited Microbial Organisms [Expert Solution]

*Streptococcus thermophilus* Strain ST6008

A sample of the *Streptococcus thermophilus* (ST) strain ST6008 has been deposited at DSMZ (Deutsche Sammlung von Mikroorganismen and Zellkulturen GmbH, Mascheroder Weg 1b, D-38124 Braunschweig, Germany) under the accession number DSM 18111 with a deposit date of 29 Mar. 2006. The deposit has been made under the conditions of the Budapest Treaty on the International Recognition of the Deposit of Microorganisms for the Purposes of Patent Procedure.

The Applicant requests that a sample of the deposited microorganisms will be made available only by the issue of a sample to an expert approved either by the Applicant and/or by the Patent Office.

Definitions

In the present context, a yogurt starter culture is a bacterial culture which comprises at least one *Lactobacillus bulgaricus* strain and at least one *Streptococcus thermophilus* strain. In accordance herewith, a yogurt is a fermented milk product obtainable by inoculating and fermenting milk with a *Lactobacillus bulgaricus* strain and a *Streptococcus thermophilus* strain.

In the present context, the term "packaging" (a suitable amount of) the fermented milk in a suitable package simply relates to the final packaging of the fermented milk to obtain a product that can be ingested by e.g. a person. It may be where the fermented milk product is a drink yogurt packaged in e.g. small container of e.g. 100 ml.

In the present context, the term "mutant" should be understood as a strain derived from a strain of the invention by means of e.g. genetic engineering, radiation and/or chemical treatment. It is preferred that the mutant is a functionally equivalent mutant, e.g. a mutant that has substantially the same Bifidobacterium growth promoting properties as the mother strain. Such a mutant is a part of the present invention. Especially, the term "mutant" refers to a strain obtained by subjecting the ST6008 strain of the invention to any conventionally used mutagenization treatment including treatment with a chemical mutagen such as ethane methane sulphonate (EMS) or N-methyl-N'-nitro-N-nitroguanidine (NTG), UV light or to a spontaneously occurring mutant.

In the present context, the term "variant" should be understood as strain which is functionally equivalent to the mother strain. For instance, a variant of ST6008 should be understood as a Streptococcus thermophilus strain which is functionally equivalent to ST6008, e.g. has the same or substantially the same Bifidobacterium growth promoting properties as the mother strain. Such a variant is a part of the present invention.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

EXAMPLES

Example 1

Growth Improvement Using *Streptococcus thermophilus* ST6008

Method and Materials

Amount of bacteria per 100 liters of milk: 10 g BB-12® of $10^{11}$ cfu/g was added to 100 liters of milk ($10^5$ ml). This results in $10^7$ cfu/g of BB-12® in the milk. For ST6008, same procedure, 2 g ST6008 having $10^9$ to $10^{10}$ cfu/g in the same 100 liters of milk, thus reaching $2\times10^4$ to $2\times10^5$ cfu/g ST6008 end concentration. For DN224, $10^{11}$ cfu/g, added 3 gram (or ml) to 100 liters ($10^5$ ml), thus $3\times10^6$ cfu/g.

Fermentation at 40° C. until reaching pH 4.55 for around 8 hours. Product is then stirred and packed into cups, then stored at +6° C. to study shelf life (up to 45 days). Experiments were done with yogurt samples of 200 ml and 3 liters scale.

TABLE 1

Yogurt cultures used in the experiments.

| Experiment name | Inoculation level of yogurt culture | Yogurt culture name | ST6008 2 g/ 100 l milk | DN224 3 g/100 l milk | Bifidobacterium BB-12® 10 g/100 l milk final |
|---|---|---|---|---|---|
| CH YT1 | 20 g/100 l milk | F-DVS YFL-702 | | | x |
| CH YT1 + DN-224 | 20 g/100 l milk | F-DVS YFL-702 | | x | x |
| Special YT including DN-224 and ST-6008 | 20 g/100 l milk | Special YT | | | x |
| CH YT1 + ST-6008 | 20 g/100 l milk | F-DVS YFL-702 | x | | x |
| CH YT2 | 20 g/100 l milk | F-DVS Y-051054 | | | x |
| CH YT2 + DN-224 | 20 g/100 l milk | F-DVS Y-051054 | | x | x |
| CH YT2 + ST-6008 | 20 g/100 l milk | F-DVS Y-051054 | x | | x |

F-DVS YFL-702 is a commercial yogurt culture available from Chr. Hansen A/S, Denmark, containing *Lactobacillus bulgaricus*, and *Streptococcus thermophilus*.

Special YT: An experimental yogurt culture containing *Lactobacillus bulgaricus*, *Streptococcus thermophilus* ST6008, *Lactococcus lactis* DN224.

F-DVS Y-051054 is a commercial yogurt culture available from Chr. Hansen A/S, Denmark containing *Lactobacillus bulgaricus*, and *Streptococcus thermophilus*.

BB-12 cell count was carried out by diluting the yogurt samples in tryptone diluent and by subsequent plating of the appropriate dilutions on non acidic MRS agar supplemented with 1% dicloxacillin (Sigma D-9016) and 1% cysteine HCl. The agar plates were incubated for 3 days at 37 degrees C. under anaerobic conditions.

Results

The results are shown in table 2.

TABLE 2

Improved growth BB-12 ® and stability in a fermented milk dairy product.

| | | D + 1 | D + 7 | D + 14 | D + 21 | D + 28 | D + 45 |
|---|---|---|---|---|---|---|---|
| 200 ml lab scale | CH YT1 | 4.30E+07 | 4.30E+07 | 4.70E+07 | 3.45E+07 | 7.50E+06 | 5.55E+06 |
| | CH YT1 + DN-224 | 1.31E+08 | 8.80E+07 | 6.70E+07 | 7.55E+07 | 3.50E+07 | 2.69E+07 |
| | Special YT incl DN-224/ST-6008 | 2.73E+08 | 2.88E+08 | 1.37E+08 | 1.22E+08 | 1.30E+08 | 8.00E+07 |
| 3 L scale | CH YT1 | 8.50E+07 | 7.40E+07 | 5.90E+07 | 6.00E+07 | 3.70E+07 | 3.20E+07 |
| | CH YT1 + DN-224 | 7.80E+07 | 9.20E+07 | 8.00E+07 | 7.20E+07 | 5.30E+07 | 2.40E+07 |
| | CH YT1 + ST-6008 | 1.37E+08 | 1.28E+08 | 1.20E+08 | 1.10E+08 | 1.04E+08 | 8.00E+07 |
| | CH YT2 | 5.60E+07 | 1.55E+07 | 1.90E+07 | 1.30E+07 | 2.45E+07 | 2.40E+07 |
| | CH YT2 + DN-224 | 1.11E+08 | 1.08E+08 | 9.20E+07 | 6.30E+07 | 5.50E+07 | 4.80E+07 |
| | CH YT2 + ST-6008 | 1.14E+08 | 1.17E+08 | 1.23E+08 | 9.60E+07 | 1.16E+08 | 5.90E+07 |
| | Special YT incl DN-224/ST-6008 | 1.19E+08 | 1.22E+08 | 1.58E+08 | 1.25E+08 | 1.38E+08 | 1.02E+08 |

The results demonstrate that ST6008 significantly improves the growth of BB-12. D+1, D+7, . . . , D+45 designate Bifidobacteria count (cfu/g) after 1, 7, . . . , 45 days of storage at +6 degrees Celsius. The result show improved BB-12 growth and stability in a fermented milk dairy product prepared with a starter culture comprising ST6008 as described herein, compared to commercially available starter cultures without ST6008. As can be seen in Table 2, when ST6008 is used one can obtain more than $10^8$ cfu/g of the *Bifidobacterium* (here BB-12).

Improved Growth of BB-12 by Addition of ST6008

Table 2 clearly shows the growth improvement effect of ST6008 in a yogurt preparation CHYT1.

In 3 Liter Scale:

As can be noticed for CHYT1, straight after day D+1, levels of BB-12 are significantly higher using ST6008 (1.37× $10^8$ cfu/g with ST6008) as compared to 7.8×$10^7$ cfu/g without ST6008. This $10^8$ cfu/g level is then further maintained to until 28 days of storage.

A similar effect is noted for CHYT2.

CONCLUSION

ST6008 improves growth of *Bifidobacterium* BB-12® during fermentation to at least $10^8$ cfu/g in fermented milk products.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

REFERENCES

1. EP111392B1
2. WO98/54337 (Chr. Hansen)
3. Saxelin M. et al.: The technology of probiotics. Trends in food science and technology, vol. 10, 1991, pages 387-392
4. Martin-Diana A. B. et al.: Development of a fermented goat's milk containing probiotic bacteria. Int. Dairy J., vol. 13, 2003, pages 827-833
5. U.S. Pat. No. 4,588,595 A (Okonogi Shigeo (JP) et al)
6. US 2005/031735 A1 (Serata Masaki (JP) et al)
7. U.S. Pat. No. 4,187,321 A (Mada Mitsuo (JP) et al)
8. U.S. Pat. No. 5,230,912 A (Yajima Masako (JP) et al)

All references cited in this patent document are hereby incorporated herein in their entirety by reference.

The invention claimed is:

1. A method for preparation of a fermented milk product, which comprises:
   i) inoculating milk with (a) a *Bifidobacterium* strain and (b) a *Streptococcus thermophilus* strain selected from the group consisting of *Streptococcus thermophilus* strain ST6008 with deposit number DSM18111 and a mutant or a variant thereof; and then
   ii) fermenting the milk,
   wherein the mutant or the variant retains substantially the same level of *Bifidobacterium* growth promoting activity as the mother strain from which the mutant or variant is obtained.

2. The method of claim 1, wherein step i) further comprises inoculating the milk with a *Lactobacillus bulgaricus* strain.

3. A method for preparation of a fermented milk product comprising at least $10^8$ cfu *Bifidobacteria* per gram fermented milk product, wherein the method comprises:
   i) inoculating milk with a culture comprising at least one *Streptococcus thermophilus* strain, at least one *Bifidobacterium* strain and optionally at least one *Lactobacillus bulgaricus* strain, wherein one of said *Streptococcus thermophilus* strain is selected from the group consisting of: *Streptococcus thermophilus* strain ST6008 with deposit number DSM18111, and a mutant or a variant thereof; and then
   ii) fermenting the milk under suitable conditions,
   wherein the mutant or the variant retains substantially the same level of *Bifidobacterium* growth promoting activity as the mother strain from which the mutant or variant is obtained.

4. The method of claim 1, for preparation of a fermented milk product comprising at least $10^8$ cfu Bifidobacteria per gram fermented milk product wherein the method comprises:
   i) inoculating milk with a yogurt culture comprising at least one *Lactobacillus bulgaricus* strain, at least one *Streptococcus thermophilus* strain and at least one *Bifidobacterium* strain, wherein one of said *Streptococcus thermophilus* strain is *Streptococcus thermophilus* strain ST6008 with deposit number DSM18111;
   ii) fermenting the milk under suitable conditions to obtain a fermented milk product with at least $10^8$ cfu *Bifidobacteria* per gram fermented milk; and
   iii) packaging a suitable amount of the fermented milk product in a suitable package.

5. The method of claim 1, wherein the *Bifidobacterium* strain belongs to a species selected from the group consisting of *Bifidobacterium adolescentis, Bifidobacterium animalis, Bifidobacterium asteroids, Bifidobacterium bifidum, Bifidobacterium breve, Bifidobacterium catenulatum, Bifidobacterium infantis, Bifidobacterium lactis, Bifidobacterium longum* and *Bifidobacterium pseudocatenulatum*.

6. The method of claim 1, wherein the *Bifidobacterium* strain is a strain of *Bifidobacterium animalis* subspecies *lactis*.

7. The method of claim 1, wherein the *Bifidobacterium* strain is selected from the group consisting of CHCC5445 with deposit number DSM15954, and CHCC7158 with deposit number DSM17280.

8. The method of claim 1, wherein the fermented milk product contains at least $10^8$ cfu *Bifidobacteria* per gram fermented milk product.

9. The method of claim 1, wherein the fermented milk product contains at least $10^8$ cfu/g Bifidobacteria after 28 days of storage at +6° C.

10. The method of claim 1, wherein in step i) the milk is inoculated with from $10^5$ to $3 \times 10^7$ cfu/g of *Bifidobacterium* and with ST6008 having deposit number DSM18111 or a mutant or variant thereof at a concentration from $10^4$ to $3.5 \times 10^6$ cfu/g.

11. The method of claim 1, wherein the milk in step i) is inoculated with $10^5$ to $3 \times 10^7$ cfu/g of the *Bifidobacterium* and/or with $10^4$ to $3.5 \times 10^6$ cfu/g of the *Streptococcus thermophilus*.

12. The method of claim 1, wherein in step i) the milk is further inoculated with at least one *Lactococcus lactis* subs. *lactis* strain selected from the group consisting of *Lactococcus lactis* subs. *lactis* DN224 with deposit number DSM11037, and *Lactococcus lactis* subs. *lactis* DN223 with deposit number DSM11036.

13. The method of claim 1, wherein the fermented milk product is a yogurt.

14. The method of claim 1, wherein the fermented milk product is packaged in a sealed package that contains from 25 to 3000 ml of the product.

15. A culture comprising:
i) from $10^5$ to $10^{12}$ cfu/g of a strain with deposit number DSM15954 and
ii) from $10^5$ to $10^{12}$ cfu/g ST6008 with deposit number DSM18111.

16. The culture of claim 15, which further comprises:
iii) from $10^5$ to $10^{12}$ cfu/g of DN224 with deposit number DSM 11037 or DN223 with deposit number DSM 11036.

17. A fermented milk product obtainable by the method of claim 1.

18. A fermented milk product comprising a *Streptococcus thermophilus* strain selected from the group consisting of ST6008 with deposit number DSM18111, and a mutant or a variant thereof,
wherein the mutant or the variant retains substantially the same level of *Bifidobacterium* growth promoting activity as the mother strain from which the mutant or variant is obtained.

19. The fermented milk product of claim 1, which comprises $10^3$ to $10^{10}$ cfu/g of the *Streptococcus thermophilus* strain.

20. The fermented milk product of claim 1, which further comprises $10^3$ to $10^{10}$ cfu/g of Bifidobacteria and/or from $10^3$ to $10^{10}$ cfu/g of a *Lactococcus lactis* subs. *lactis* strain.

21. A *Streptococcus thermophilus* strain selected from the group consisting of ST6008 with deposit number DSM18111, and a mutant or a variant thereof,
wherein the mutant or the variant retains substantially the same level of *Bifidobacterium* growth promoting activity as the mother strain from which the mutant or variant is obtained.

22. The strain of claim 21 in isolated form.

23. The method of claim 1, wherein the method further comprises adding additional microorganisms or additives to the fermented milk.

24. The method of claim 1, wherein the method further comprises packaging the fermented milk product.

25. The method of claim 3, wherein the method further comprises packaging a suitable amount of the fermented milk product in a suitable package.

* * * * *